United States Patent
Hsieh et al.

(10) Patent No.: US 10,421,827 B2
(45) Date of Patent: Sep. 24, 2019

(54) METHOD FOR MANUFACTURING FILTER MEMBRANE FOR INHIBITING MICROORGANISMS

(71) Applicants: MIPTECH CO., LTD., Miaoli County (TW); Kuo-Chih Hsieh, Taipei (TW)

(72) Inventors: Kuo-Chih Hsieh, Taipei (TW); Chien-Ying Tsai, New Taipei (TW)

(73) Assignees: MIPTECH CO., LTD., Miaoli County (TW); Kuo-Chih Hsieh, Taipei (TW)

( * ) Notice: Subject to any disclaimer, the term of this patent is extended or adjusted under 35 U.S.C. 154(b) by 119 days.

(21) Appl. No.: 15/678,120

(22) Filed: Aug. 16, 2017

(65) Prior Publication Data

US 2019/0055327 A1 Feb. 21, 2019

(51) Int. Cl.
| | |
|---|---|
| *C08F 8/42* | (2006.01) |
| *A01N 59/16* | (2006.01) |
| *A01N 25/10* | (2006.01) |
| *C08G 75/23* | (2006.01) |
| *C08J 5/18* | (2006.01) |
| *B01D 69/02* | (2006.01) |
| *B01D 67/00* | (2006.01) |
| *B01D 69/14* | (2006.01) |
| *B01D 71/78* | (2006.01) |

(Continued)

(52) U.S. Cl.
CPC ............... *C08F 8/42* (2013.01); *A01N 25/10* (2013.01); *A01N 59/16* (2013.01); *B01D 67/002* (2013.01); *B01D 69/02* (2013.01); *B01D 69/141* (2013.01); *B01D 69/148* (2013.01); *B01D 71/78* (2013.01); *B01D 71/82* (2013.01); *C08G 75/23* (2013.01); *C08J 5/18* (2013.01); *B01D 71/022* (2013.01); *B01D 2313/12* (2013.01); *B01D 2325/48* (2013.01); *C08G 2340/00* (2013.01); *C08J 2327/06* (2013.01); *C08J 2327/16* (2013.01); *C08J 2333/20* (2013.01); *C08J 2339/06* (2013.01); *C08J 2381/06* (2013.01)

(58) Field of Classification Search
CPC ......... A01N 59/16; B01D 71/022; C08J 3/20; C08J 3/201
See application file for complete search history.

(56) References Cited

PUBLICATIONS

Isawi et al. Applied Surface Science 38, 268-281 (Year: 2016).*

(Continued)

*Primary Examiner* — Mark S Kaucher
(74) *Attorney, Agent, or Firm* — Leong C. Lei

(57) ABSTRACT

A method for manufacturing a filter membrane for inhibiting microorganisms includes the following steps: obtaining a nano-zinc precursor and dissolving it into water, adding at least one reducing agent and interfacial agent to the water, thereby reducing zinc ions of the nano-zinc precursor to zinc particles so as to form liquid having nano-zinc particles; respectively placing the liquid having nano-zinc particles and a polymer material into plastic masterbatch process equipment, respectively volatilizing the fluid having nano-zinc particles and polymer material through the plastic masterbatch process equipment, performing air extraction and mixing by the plastic masterbatch process equipment, and adding at least one grafting agent to perform a mixed graft link, allowing the nano-zinc particles and polymer material to be linked together stably so as to form a plastic masterbatch having nano-zinc particles; and making the plastic masterbatch into a filer membrane through film making equipment.

11 Claims, 9 Drawing Sheets

(51) Int. Cl.
*B01D 71/82* (2006.01)
*B01D 71/02* (2006.01)

(56) References Cited

PUBLICATIONS

Jo et al. Ind. Eng. Chem.Res., 55, 7801-7809 (Year: 2016).*
Pascual et al. Appl. Mater. Interfaces, 6, 3729-3741 (Year: 2014).*
Zhao et al. Journal of Membrane Science 478, 105-116 (Year: 2015).*

* cited by examiner

ZnO grafted on PVDA(using MA)

ZnO grafted on PES(using MA)

ZnO grafted on PAN(using MA)

ZnO grafted on PVC(using MA)

Test Report  No. : CM/2015/10278   Date : 2015/02/09   Page : 2 of 3

UNITIVA APPLIED MATERIALS CORP.
8F., NO. 67, CHANGCHUN RD., ZHONGSHAN DIST., TAIPEI CITY 10447, TAIWAN

Test Result(s)

PART NAME No.1      :   BLACK PLASTIC PELLETS

| Test Item(s) | Unit | Method | MDL | Result No.1 |
|---|---|---|---|---|
| Zinc (Zn) | % | ICP-AES after as per acid digestion. | 0.0002 | 1.27 |

Note :
1. mg/kg = ppm ; 0.1wt% = 1000ppm
2. n.d. = Not Detected
3. MDL = Method Detection Limit This document is issued by the Company subject to its General Conditions of Service printed overleaf, available on request or accessible at http://www.sgs.com/en/Terms-and-Conditions.asgx and, for electronic format documents, subject to Terms and Conditions for Electronic Documents at http://www.sgs.com/en/Terms-and-Conditions/Terms-Documnet.asgx. Attention is drawn to the limitation of liability, indemnification and jurisdiction issues defined therein. Any holder of this document is advised that information contained hereon reflects the Company's findings at the time of its intervention only and within the limits of client's instruction, if any. The Company's sole responsibility is to tis Client and this document does not exonerate parties to a transaction from exercising all their rights and obligations under the transaction documents. This document cannot be reproduced, except in full, without prior written approval of the Company. Any unauthorized alteration, forgery or falsification of the content or appearance of this document is unlawful and offenders may be prosecuted to the fullest extent of the law. Unless otherwise stated the results shown this test report refer only to the sample(s) tested.

SGS Taiwan Ltd.

33, Wu Chuan Rd., New Taipei industrial Park, New Taipei Ctity
t+886 (02)2299 3279 f+886 (02)2299 3237 www.sgs.tw Member of the SGS Group

FIG.9

Test Report

No. : CM/2015/40195    Date : 2015/04/27    Page : 2 of 3

UNITIVA APPLIED MATERIALS CORP.
8F., NO. 67, CHANGCHUN RD., ZHONGSHAN DIST., TAIPEI CITY 10447, TAIWAN

Test Result(s)

PART NAME No.1         :    WHITE FIBER

| Test Item(s) | Unit | Method | MDL | Result No.1 |
|---|---|---|---|---|
| Zinc (Zn) | mg/kg | ICP-AES after as per acid digestion. | 2 | 851 |

Note :
1. mg/kg = ppm ; 0.1wt% = 1000ppm
2. n.d. = Not Detected
3. MDL = Method Detection Limit This document is issued by the Company subject to its General Conditions of Service printed overleaf, available on request or accessible at http://www.sgs.com/en/Terms-and-Conditions.asgx and, for electronic format documents, subject to Terms and Conditions for Electronic Documents at http://www.sgs.com/en/Terms-and-Conditions/Terms-Documnet.asgx. Attention is drawn to the limitation of liability, indemnification and jurisdiction issues defined therein. Any holder of this document is advised that information contained hereon reflects the Company's findings at the time of its intervention only and within the limits of client's instruction, if any. The Company's sole responsibility is to tis Client and this document does not exonerate parties to a transaction from exercising all their rights and obligations under the transaction documents. This document cannot be reproduced, except in full, without prior written approval of the Company. Any unauthorized alteration, forgery or falsification of the content or appearance of this document is unlawful and offenders may be prosecuted to the fullest extent of the law. Unless otherwise stated the results shown this test report refer only to the sample(s) tested.

SGS Taiwan Ltd.    33, Wu Chuan Rd., New Taipei industrial Park, New Taipei Ctity
t+886 (02)2299 3279 f+886 (02)2299 3237 www.sgs.tw
Member of the SGS Group

FIG.10

Test Report (No.) : CM/2016/90238  (Date) : 2016/09/30  (Page) : 2 of 3

EVER PURE APPLIED MATERIALS CO., LTD.

NO. 109-1, DINGPU LI, CHUNAN TOWN, MIAO-LI COUNTY 35051, TAIWAN(R.O.C.)

(Test Results)

(PART NAME)No. 1 : (WHITE FILM)

| (Test Items) | (Unit) | (Method) | (MDL) | (Result) No. 1 |
|---|---|---|---|---|
| Zinc (Zn) | mg/kg | ICP-AES after as per acid digestion. | 2 | 845 |

(Note):
1. mg/kg = ppm ; 0.1wt% = 1000ppm
2. n.d. = Not Detected
3. MDL = Method Detection Limit This document is issued by the Company subject to its General Conditions of Service printed overleaf, available on request or accessible at http://www.sgs.com/en/Terms-and-Conditions.asgx and, for electronic format documents, subject to Terms and Conditions for Electronic Documents at http://www.sgs.com/en/Terms-and-Conditions/Terms-Documnet.asgx. Attention is drawn to the limitation of liability, indemnification and jurisdiction issues defined therein. Any holder of this document is advised that information contained hereon reflects the Company's findings at the time of its intervention only and within the limits of client's instruction, if any. The Company's sole responsibility is to tis Client and this document does not exonerate parties to a transaction from exercising all their rights and obligations under the transaction documents. This document cannot be reproduced, except in full, without prior written approval of the Company. Any unauthorized alteration, forgery or falsification of the content or appearance of this document is unlawful and offenders may be prosecuted to the fullest extent of the law. Unless otherwise stated the results shown this test report refer only to the sample(s) tested.

SGS Taiwan Ltd.    33, Wu Chuan Rd., New Taipei industrial Park, New Taipei Ctity
t+886 (02)2299 3279 f+886 (02)2299 3237 www.sgs.tw Member of the SGS Group

FIG. 11

Test Report     (No.) : CM/2016/90240     (Date) : 2016/09/30     (Page) : 2 of 3

EVER PURE APPLIED MATERIALS CO., LTD.

NO.109-1, DINGPU LI, CHUNAN TOWN, MIAO-LI COUNTY 35051, TAIWAN(R.O.C.)

(PART NAME)No.1     :     (WHITE LIQUID)

| (Test Items) | (Unit) | (Method) | (MDL) | (Result) No.1 |
|---|---|---|---|---|
| Zinc (Zn) | mg/kg | ICP-AES after as per acid digestion. | 2 | 3 |

(Note):
1. mg/kg = ppm ; 0.1wt% = 1000ppm
2. n.d. = Not Detected
3. MDL = Method Detection Limit This document is issued by the Company subject to its General Conditions of Service printed overleaf, available on request or accessible at http://www.sgs.com/en/Terms-and-Conditions.asgx and, for electronic format documents, subject to Terms and Conditions for Electronic Documents at http://www.sgs.com/en/Terms-and-Conditions/Terms-Documnet.asgx. Attention is drawn to the limitation of liability, indemnification and jurisdiction issues defined therein. Any holder of this document is advised that information contained hereon reflects the Company's findings at the time of its intervention only and within the limits of client's instruction, if any. The Company's sole responsibility is to tis Client and this document does not exonerate parties to a transaction from exercising all their rights and obligations under the transaction documents. This document cannot be reproduced, except in full, without prior written approval of the Company. Any unauthorized alteration, forgery or falsification of the content or appearance of this document is unlawful and offenders may be prosecuted to the fullest extent of the law. Unless otherwise stated the results shown this test report refer only to the sample(s) tested.

SGS Taiwan Ltd.     33, Wu Chuan Rd., New Taipei industrial Park, New Taipei Ctity
t+886 (02)2299 3279 f+886 (02)2299 3237 www.sgs.tw
Member of the SGS Group

FIG.12

METHOD FOR MANUFACTURING FILTER MEMBRANE FOR INHIBITING MICROORGANISMS

(a) TECHNICAL FIELD OF THE INVENTION

The present invention relates to a method for manufacturing a filter membrane for inhibiting microorganisms, and more particularly to a method for manufacturing a filter membrane for inhibiting microorganisms, including the following steps: reducing first to obtain nano-zinc particles: adding at least one reducing agent and at least one interfacial agent into water in which a nano-zinc precursor is dissolved, allowing zinc ions of the nano-zinc precursor to be reduced to zinc particles so as to obtain liquid having nano-zinc particles; forming further a plastic masterbatch having nano-zinc particles by means of air extraction and mixing: respectively processing the fluid having nano-zinc particles and polymer material to be in a volatile state through plastic masterbatch process equipment, performing the mixing in the process of air extraction, and adding at least one grafting agent to perform a mixed graft link, allowing the nano-zinc particles and polymer material to be linked together stably so as to form a plastic masterbatch having nano-zinc particles; and making the plastic masterbatch having nano-zinc particles into a filer membrane having nano-zinc particles through film making equipment, allowing a filter membrane with nano-zinc particles to be used to filter liquid or gas, and be anti-bacterial and capable of inhibiting the growth of bacteria.

(b) DESCRIPTION OF THE PRIOR ART

Zinc is strong antibiotic nutrition; it is a trace of nutrients. Zinc is an antioxidant ingredient of the human body, including four zinc atoms capable of protecting cell membrane and tissue from being damaged by hydroxyl free radicals such that it has a detoxification function and antibacterial effect. In addition, Zinc can change the metabolism of bacterial sources, making the revival chance of bacteria much less such that it can prevent the formation of many bacteria.

Therefore, Zinc has been proved that it can promote bacterial cell apoptosis such that some companies has developed combining zinc with articles so as to make the articles in combination with zinc antibacterial and bacteriostatic.

Taking zinc in combination with plastics as an example, conventional methods for combining zinc with plastics mainly are: adding first a plastic masterbatch into an organic solvent, allowing the plastic masterbatch to be dissolved in the organic solvent so as to form a plastic solution; adding zinc into the plastic solution to mix therewith; and placing the plastic solution with zinc into plastic granulation equipment to make plastic particles with zinc finally.

Thereafter, the plastic particles having zinc are used to make many kinds of articles (e.g. textile products, containers and the like), obtaining the articles made from plastic solution having zinc, thereby allowing them to have anti-bacterial and bacteriostatic effects.

However, in conventional methods for combining zinc elements with plastics, the plastic solution is a thick and dense liquid after the plastic masterbatch is dissolved such that zinc elements may not be mixed uniformly with the plastic solution. In addition, zinc elements in conventional methods are ionized, which further causes zinc elements not to be able to be linked stably with the plastic solution. As a result, articles made from conventional plastic solution having zinc elements (e.g. textile products) are very easy to lose zinc elements gradually after water wash, which causes the antibacterial or bacteriostatic capacity of the articles to be lowered or even lost. For example, a filter film having zinc can be reached more than standard 600 ppm per particle in initial concentration, but it will be less than 600 ppm per particle after scoured by water current for a long time.

Furthermore, Chinese Patent No. CN102205209B discloses "antibacterial polymer ultra-filtration membrane and preparation method thereof", having steps mainly preparing a film-forming polymer solution; adding antibacterial agent particles having a long-term sustained release function formed by compounding an inorganic carrier (e.g. zeolite) and antibacterial agent (e.g. zinc ions) into the film-forming polymer solution, where the antimicrobial agent particles having a long-term sustained release function formed by compounding the inorganic carrier and antibacterial agent occupies 0.01 to 0.1% by weight based on the weight of the polymers in the film-forming polymer solution, where the particle size of the antibacterial agent particle is 0.01-10 μm; and preparing the antibacterial polymer ultra-filtration membrane through the non-solvent induced phase separation (NIPS) or thermally induced phase separation process (TIPS) by means of dry-wet spinning or wet spinning. The ultra-filtration membrane formed by the above method can be used for water filtration and purification, and has a long-term antibacterial effect; it can be widely used in drinking water treatment, home water purifier filter, and food and drug filtration and purification.

However, in the above patent, antibacterial agents such as sliver, copper and zinc will be dissolved and ionized, and lost substantially in a water bath stage of phase change in the process of mixing the inorganic antibacterial agent using powder such as zeolite as a carrier in the film-forming solution, resulting in an inability to accurately control the proper equivalent of the antimicrobial agent contained in the filter membrane; the inorganic bacterial agent using powder such as zeolite as a carrier, in the above patent, is added in a homogeneous casting solution, and the powder will then be precipitated in the process of standing defoaming, which affects the homogeneity of the casting solution, resulting in the lack of consistency in the equivalent of the antibacterial agent contained in the filter membrane. Meanwhile, it is difficult to ensure the dispersibility of fine powders; the physical characteristics and filtration precision of the filter membrane will be changed, affecting the use efficiency thereof in the condition of powder agglomeration.

SUMMARY OF THE INVENTION

To overcome the defects mentioned above, the present invention is proposed.

The present invention proposes a method for manufacturing a filter membrane for inhibiting microorganisms, including the following steps: obtaining a nano-zinc precursor and dissolving it into water, adding at least one reducing agent and at least one interfacial agent to the water in which the nano-zinc precursor is dissolved, thereby reducing zinc ions of the nano-zinc precursor to zinc particles so as to form liquid having nano-zinc particles; respectively placing the liquid having nano-zinc particles and a polymer material into plastic masterbatch process equipment, respectively processing the fluid having nano-zinc particles and the polymer material to be in a volatile state through the plastic masterbatch process equipment, performing air extraction and mixing by the plastic masterbatch process equipment, and adding at least one grafting agent to perform a mixed graft link, allowing the nano-zinc particles and polymer material to be linked together stably so as to form a plastic masterbatch having nano-zinc particles; and making the plastic masterbatch having nano-zinc particles into a filer membrane having nano-zinc particles through film making equipment.

The present invention is characterized in that the nano-zinc precursor is first reduced to nano-zinc particles, which uses a reducing agent to reduce nano-zinc ions to the nano-zinc particles, and an interfacial agent is then used to be in combination with nano-zinc particles by means of chemical grafting, allowing the reduced nano-zinc particles not to be in combination with other particles (i.e. preventing secondary agglomeration from being generated among the nano-zinc particles), thereby generating stable reduced nano-zinc particles; thereafter, a plastic masterbatch having nano-zinc particles is formed by means of air extraction and mixing, which uses plastic masterbatch process equipment to respectively process a liquid having nano-zinc particles and polymer material to be in a volatile state, and mix them in the process of air extraction, allowing the nano-zinc particles to be linked uniformly and stably with the polymer material so as to form a plastic masterbatch having nano-zinc particles; finally, the plastic masterbatch having nano-zinc particles is made into a filter membrane having nano-zinc particles through film making equipment.

Therefore, the filter membrane having nano-zinc particles made from the plastic masterbatch having nano-zinc particles can be used for the filtration of liquid or gas; zinc particle being antibacterial allows the filter membrane having nano-zinc particles to be capable of decomposition of bacteria and inhibition of bacterial growth. In addition, nano-zinc particles being stably linked with polymer material allows nano-zinc particles not to be easy to be lost gradually from the filter membrane having nano-zinc particles due to solution, phase change or water wash, capable of maintaining the antibacterial capacity of the filter membrane effectively for a long time.

BRIEF DESCRIPTION OF THE DRAWINGS

FIG. 9 is a first test report of the method for manufacturing a filter membrane for inhibiting microorganisms of the present invention;

FIG. 10 is a second test report of the method for manufacturing a filter membrane for inhibiting microorganisms of the present invention;

FIG. 11 is a third test report of the method for manufacturing a filter membrane for inhibiting microorganisms of the present invention; and FIG. 12 is a fourth test report of the method for manufacturing a filter membrane for inhibiting microorganisms of the present invention.

DETAILED DESCRIPTION OF THE PREFERRED EMBODIMENTS

Figure 1:
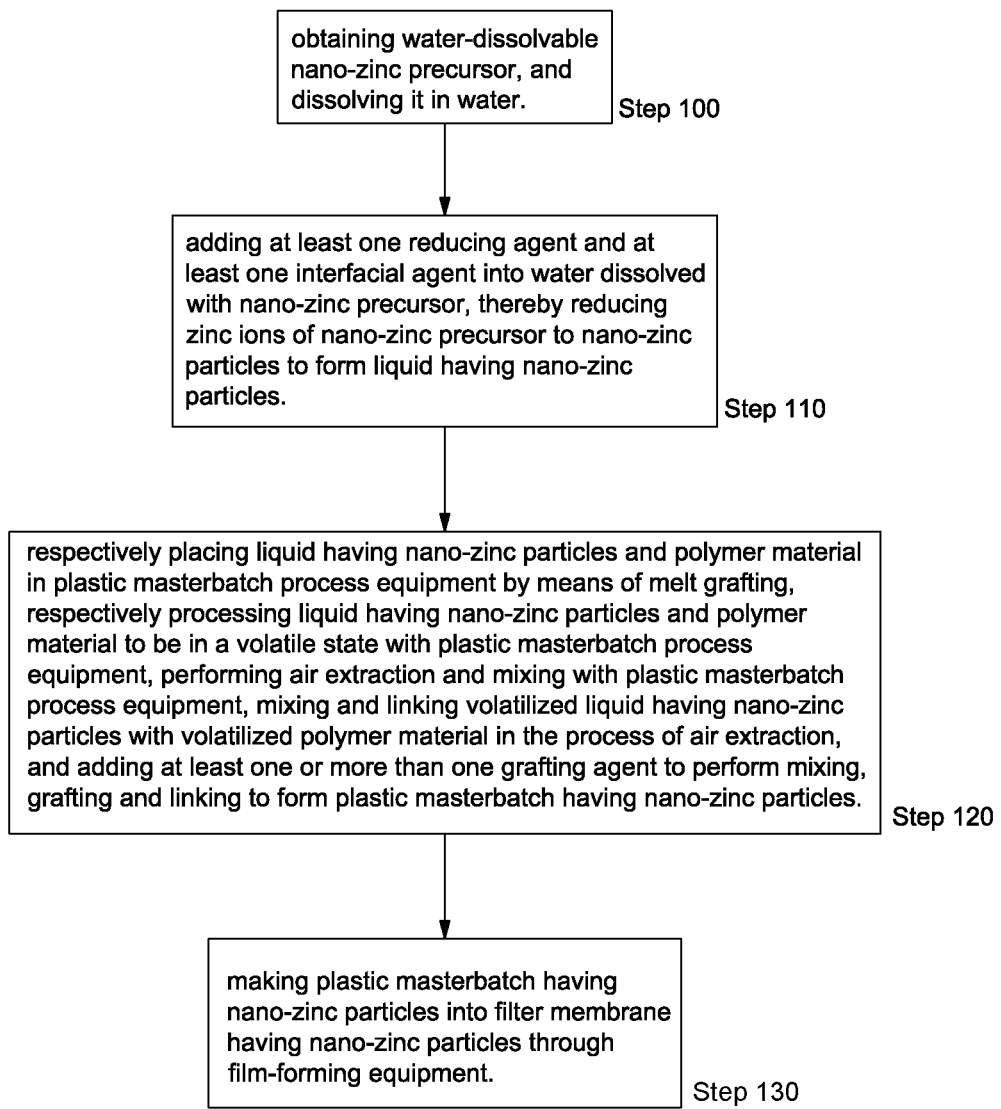
FIG. 1 is a flow chart of a method for making a filter membrane for inhibiting microorganisms of the present invention.

Referring to FIG. 1, a method for manufacturing a filter membrane for inhibiting microorganisms of the present invention includes the following steps:

step 100: obtaining a nano-zinc precursor capable of being dissolved in water, and dissolving the nano-zinc precursor into water, where the nano-zinc precursor may be zinc chloride, zinc gluconate, zinc acetate, zinc sulfate or zinc carbonate capable of being dissolved in water; for example, zinc dioxide being dissolved in water: $Zn^{2+}(s)+2e^- \rightarrow Zn$ (aq)

step 110: adding at least one reducing agent and at least one interfacial agent into the water in which the nano-zinc precursor is dissolved, thereby reducing the zinc ions of the nano-zinc precursor to nano-zinc particles so as to form a liquid having nano-zinc particles; namely, reducing nano-zinc ions to nano-particles with the reducing agent, and then using the interfacial agent to be in combination with the nano-zinc particles by means of chemical grafting, allowing the reduced nano-zinc particles not to be in combination with other particles (i.e. preventing secondary agglomeration from being generated among the nano-zinc particles), thereby forming the reduced stable nano-zinc particles, where the reducing agent may be one or more than one selected from a group constituted by hydrazine compounds, dextrose, sodium ascorbate and ascorbic acid, sodium carboxymethyl celluiose (CMC), $SO_2$, $NaBH_4$, and the like.

The interfacial agent may be one or more than one selected from a group constituted by cetyl trimethylammonium bromide (CTAB), sodium dodecyl sulfate (SDS), polyvinylpyrrolidone (PVP), 3-(trimethoxysilyl)propyl methacrylate, sodium hydrogen methylsulfonate (MSMA), Dibenzoyl-L-tartaric acid (DBTA), 3-aminopropyltrimethoxy-silane (APTMS), (3-Mercaptopropyl)trimethoxysilane (MPTMS).

step 120: respectively placing the liquid having nano-zinc particles and a polymer material into plastic masterbatch process equipment by means of melt grafting, respectively processing the liquid having nano-zinc particles and polymer material to be in a volatile state through the plastic masterbatch process equipment, performing air extraction and mixing with the plastic masterbatch process equipment, allowing the volatilized liquid having nano-zinc particles and volatilized polymer material to be added with at least one grafting agent so as to carry out a mixed graft link in the process of air extraction, thereby forming a plastic masterbatch having nano-zinc particles, where the polymer material may be plastics such as PET, PA6(NYLON), PP, PE, ABS, PC, PVDF, PS, PES, PVC, PAN, and the like.

step 130: making the plastic masterbatch having nano-zinc particles into a filter membrane having nano-zinc particles through film making equipment.

Figure 2:
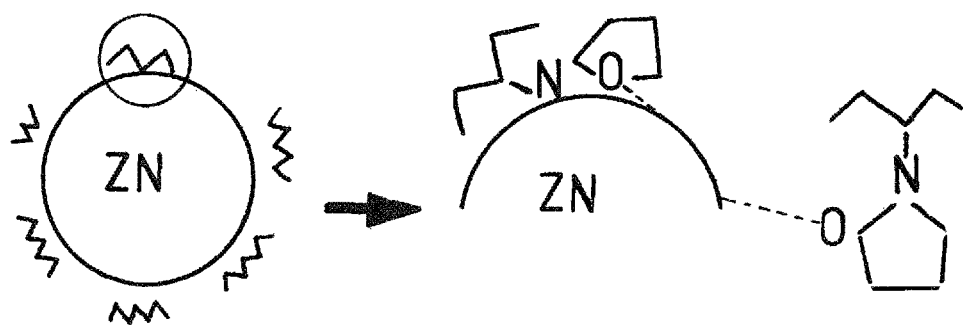
FIG. 2 shows a chemical formula of a nano-zinc being grafted on polyvinyl pyrrolidone (PVP)
Figure 3:
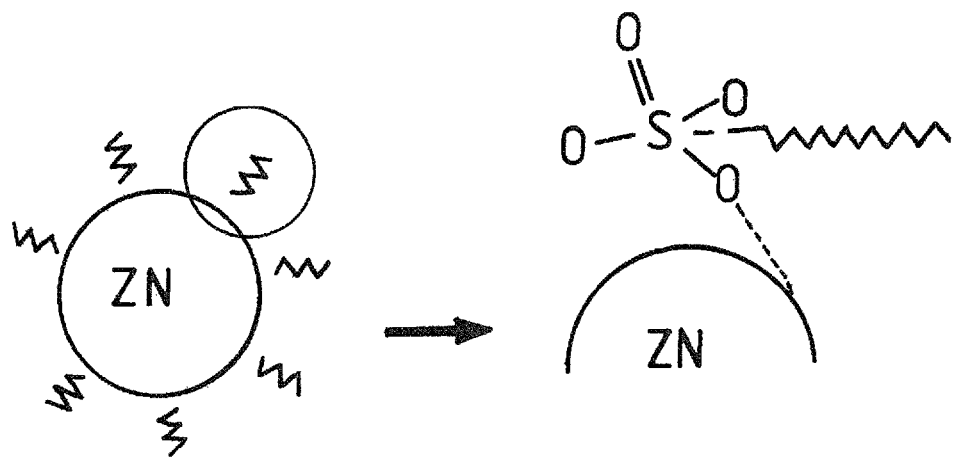
FIG. 3 shows a chemical formula of a nano-zinc being grafted on sodium dodecyl sulfate (SDS)

In the step 110, the interfacial agent grafting the nano-zinc particles by means of chemical grafting in the process of nano-zinc particle being linked with the interfacial agent is a modification process, which allows the nano-zinc particles not to be liked with other particles. Furthermore, the nano-zinc particles are then formed into a composite material after the nano-zinc particles interact with the interfacial agent through chemical grafting process. For example, after PVP interacts with the nano-zinc particle after chemical grafting process, the chemical formula thereof is shown in FIG. 2, and after SDS interacts with the nano-zinc particles through chemical grafting process, the chemical formula thereof is shown in FIG. 3.

In the step 110, when CMC is selected for the interfacial agent, with CMC being dissolvable in water solution to cause it to be sticky and thick, allowing the nano-zinc particles to move more slowly in the sticky and thick water solution so that the chance of the collision and agglomeration thereof is reduced, thereby stabilizing them. In addition, the size distribution of the nano-zinc particles can be changed by changing temperature and/or adjusting the concentration of the reducing agent, achieving the purpose of handling particle size.

Figure 4:
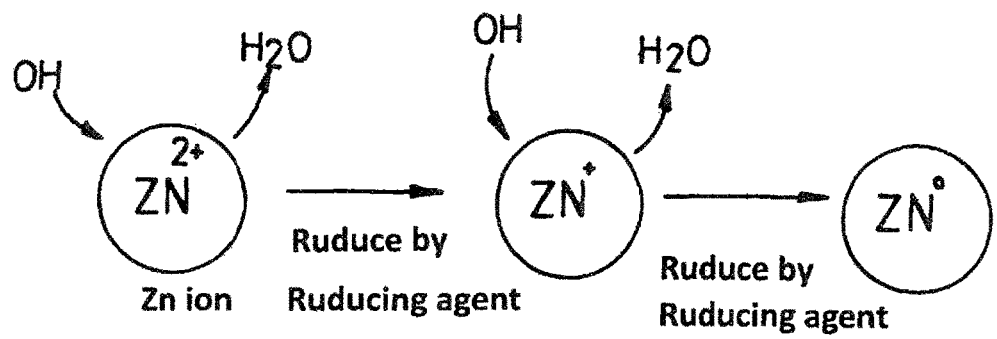
FIG. 4 shows a process of a zinc ion of a nano-zinc precursor being reduced to a nano-zinc particle.

In a first preferred embodiment of the present invention, the zinc ions of the nano-zinc precursor being reduced to the nano-zinc particles in the step 110 is specifically described. The zinc ions of $Zn^{+2}$ concentration ranged from $1\times10^{-5}$ mole to $1\times10^{-3}$ mole are placed in a glass bottle, deionized water (DI) is added in the bottle, and the concentration of sodium dodecyl sulfatethe (SDS) is set to be ranged from 1 mM to 10000 mM, the concentration of cetyltrimethylammonium bromide (CTAB) from 1 mM to 10000 mM, the concentration of sodium carboxymethylcellulose (CMC) from 1 to 20 wt %. Thereafter, a solution in which a reducing agent $Na_2S_2O_5$ is ranged from 1 to 5 grams and a strong reducing agent $NaBH_4$ from 0.01 to 10M is added after stirred uniformly with a heating stirrer. In the process of stirring, the reducing agents are respectively added in. At this point, it should be noted that if the reducing agent has a high pH value, 0.1 to 40 μl of concentrated hydrochloric acid is needed to drop in; at this point, the pH value of the solution is adjusted to about 1 to 5, and the solution is stirred continuously and placed into a hot water bath of temperature ranged from 50 to 90 degrees centigrade, and heated and stirred with a magnet electric heating stirrer, thereby reducing nano-zinc ions to nano-zinc particles, the process of which is shown in FIG. 4.

In a second preferred embodiment of the present invention, the zinc ions of the nano-zinc precursor being reduced to the nano-zinc particles is further specifically described. A sonochemical method (i.e. the use of ultrasound to promote the reduction) is used; the nano-zinc precursor is placed in a reaction bottle, and the reaction bottle is then placed in a ultrasonic oven, using ultrasonic oscillation to generate reduced free radicals to reduce metal ions so as to generate nano-zinc particles. Furthermore, metal salt aqueous solution is then placed in the reaction bottle, and the interfacial agent is added therein to stabilize the nano-zinc particles. Thereafter, the reaction bottle is placed in a ultrasonic oscillator and oscillated thereby, and the reaction is completed after 8 to 15 minutes to obtain the nano-zinc particles; the reaction mechanism thereof is $H_2O \rightarrow$ —H+—OH (sonolysis)-OH(—H)+RH$\rightarrow$—R (reducing species)+$H_2O$ ($H_2$)RH$\rightarrow$—R (reducing species)+-H (sonolysis)-R(reducing species)+Zn(M−1)++H++R+. The driving force of this reaction mechanism comes from air pockets generated from shock waves, or .OH or .H formed between air pockets and the solution, and the reduction of carbon chain molecules generates .R free radicals; or RH between interfaces is oscillated to form .R free radicals, which have redox reaction with metal ions to reduce the metal ions to metal nanoparticles of zero-valence.

In a third preferred embodiment of the present invention, the zinc ions of the nano-zinc precursor being reduced to the nano-zinc particles is further specifically described. An electrochemical method is used; this electrochemical method is published by Reetz, M. T. and Helbig, W. in year 1994, being used to generate metal nano-particles, the sizes of which can be adjusted by controlling the current of electrolytic apparatus. Therefore, the present invention can use the electrochemical method to reduce the zinc ions of the nano-zinc precursor to nano-zinc particles; the process thereof is shown as the following:

Anode: $Met_{bulk} \rightarrow Met^{n+} + n\ e^-$

Cathode: $Met^{n+} + n\ e^- + stabilizer \rightarrow$ $Met_{coll}/stabilizer$

Sum: $Met_{bulk} + stabilizer \rightarrow$ $Met_{coll}/stabilizer$

In the step 120, the melt grafting is to place the liquid having nano-zinc particles and a polymer material respectively in a plastic masterbatch process equipment, which has twin screw extraction mechanism and at least six suction holes, where the twin screw extraction mechanism is in a vacuum state. The liquid having nano-zinc particles and the polymer material are respectively placed in the plastic masterbatch process equipment, where the liquid having nano-zinc particles and polymer material have a weight ratio ranged between 1:10 and 1:1. Whereby, the liquid having nano-zinc particles and polymer material are respectively processed to be in a volatile state with the plastic masterbatch process equipment, allowing the volatilized liquid having nano-zinc particles and volatilized polymer material to be mixed and linked together through the twin screw extraction and six suction holes in the process of air extraction. At this point, at least one grafting agent is added therein to perform the mixed graft link, thereby forming a plastic masterbatch having nano-zinc particles, where the addition amount of the grafting agent is between 0.1% and 5% by weight based on the weight percent of the polymer material weight.

The grafting agent may be maleic anhydride (MAA), which has a molecular formula $C_4H_2O_3$ and chemical formula

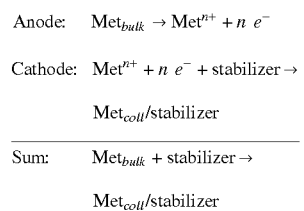

The grafting agent may also be glycidyl methacrylate (GMA), which has a molecular formula $C_7H_{10}O_3$ and chemical formula

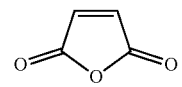

The grafting agent may also be acrylamide (AM), which has a molecular formula $CH_2$=$CHCONH_2$ and chemical formula

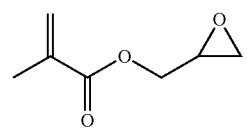

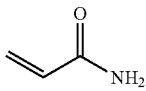

The grafting agent may also be acrylic acid (AAM), which has a molecular formula $C_3H_4O_2$ and chemical formula

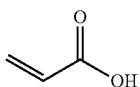

Figure 5:
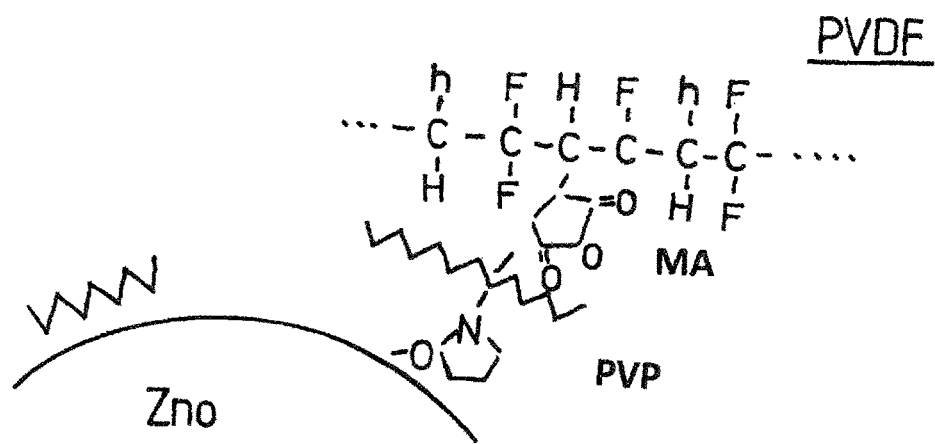
FIG. 5 shows a chemical formula of nano-zinc particle grafted on PVDF through maleic anhydride (grafting agent)
Figure 6:
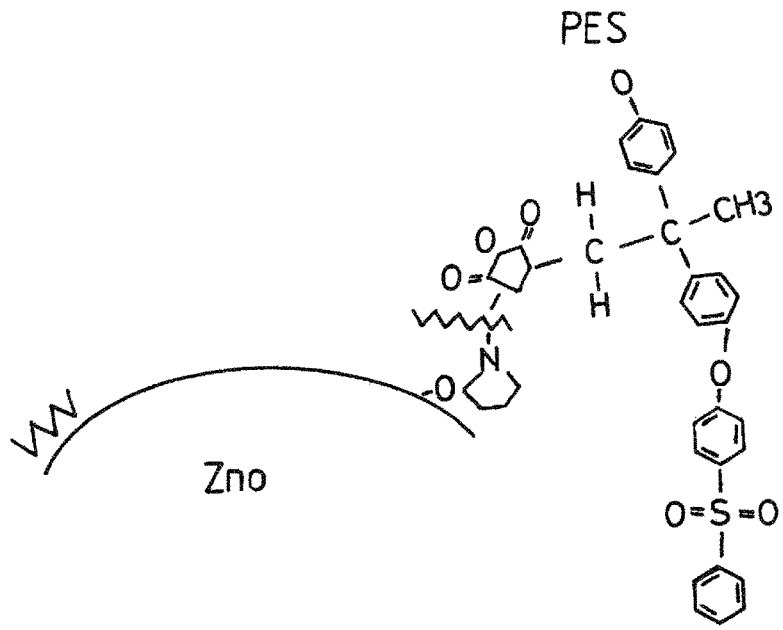
FIG. 6 shows a chemical formula of nano-zinc particle grafted on PES through maleic anhydride (grafting agent)
Figure 7:
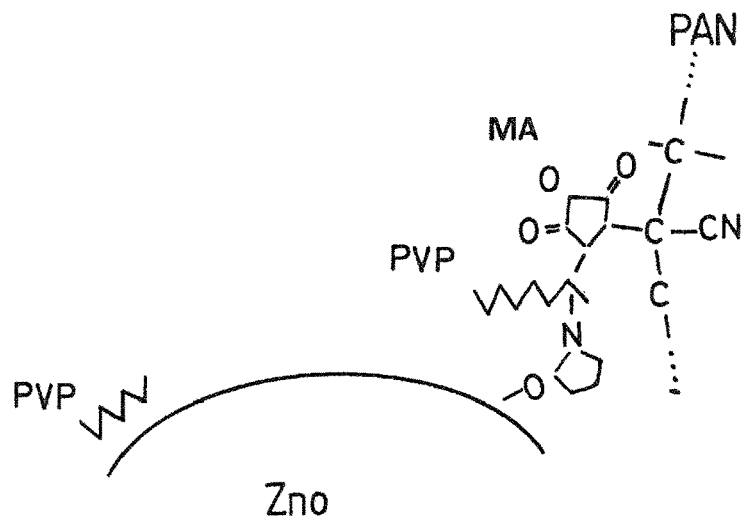
FIG. 7 shows a chemical formula of nano-zinc particle grafted on PAN through maleic anhydride (grafting agent)
Figure 8:
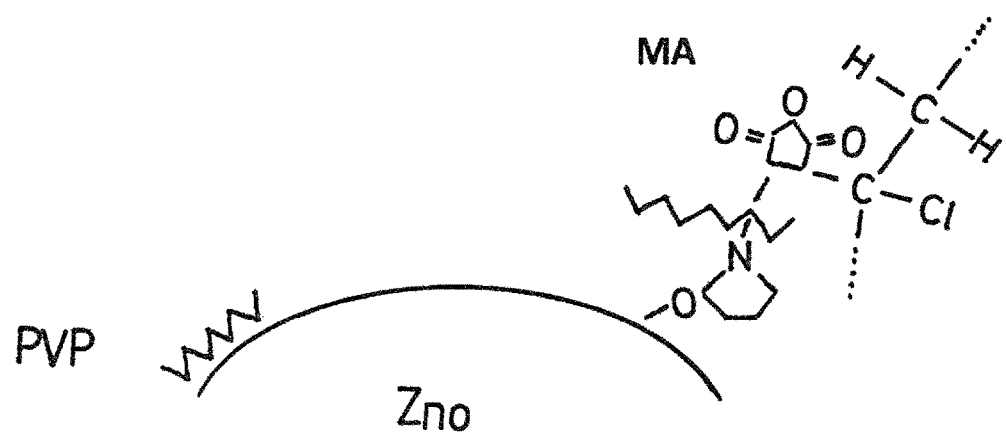
FIG. 8 shows a chemical formula of nano-zinc particle grafted on PVC through maleic anhydride (grafting agent)

In a preferred embodiment, the chemical formulae for the nano-zinc particles of the present invention grafted on PVDF, PES, PAN, and PVC are explained, where FIG. 5 shows a formula for the nano-zinc particle of the present invention being grafted on PVDF through maleic anhydride (MAA); FIG. 6 shows a formula for the nano-zinc particle of the present invention added being grafted on PES through maleic anhydride (MAA); FIG. 7 shows a formula for the nano-zinc particle of the present invention being grafted on PAN through maleic anhydride (MAA); and FIG. 8 shows a formula for the nano-zinc particle of the present invention being grafted on PVC through maleic anhydride (MAA).

Therefore, the present invention is featured in that a nano-zinc precursor is first reduced to obtain nano-zinc particles, nano-zinc ions being reduced to nano-zinc particles with a reducing agent, an interfacial agent is used to be linked with the nano-zinc particles by means of chemical grafting, allowing the reduced nano-zinc particles not to be in combination with other particles any more, preventing secondary agglomeration from being generated among nano-zinc particles, thereby obtaining the stable reduced nano-zinc particles; thereafter, at least one grafting agent is then added to perform a mixed graft link to form a plastic masterbatch having nano-zinc particles by means of melt grafting, which is to use plastic masterbatch process equipment to respectively process the liquid having nano-zinc particles and a polymer material to be in a volatile state, and mix them in the process of air extraction, allowing the nano-zinc particles to be linked with the polymer material uniformly and stably to form a plastic masterbatch having nano-zinc particles; finally, the plastic masterbatch having nano-zinc particles is made into a filter membrane having nano-zinc particles through film making equipment. Here, the filter membrane having nano-zinc particles so made is a hollow fiber filter membrane, a plate filer membrane or other type of filter membrane.

It should be noted that using the melt grafting manner allows the nano-zinc particles to be linked with polymers without affecting the mechanical properties of polymers, and even allows plastics to have very good physical performance, for example, the improvement of ductility and toughness. Therefore, the present invention can prevent the defects generated from traditional manufacturing in which any type of organic or inorganic antibacterial agent is added in casting solution; the present invention has grafted nano-zinc particles on the polymer material before film-forming, allowing the polymer material to be formed into a homogeneous casting solution after dissolved in a film-forming solution such as DMF, DMAC or NMP, preventing effectively the serious issue of the uneven dispersion or agglomeration of the antibacterial agent. Furthermore, the casting solution is allowed to reduce effectively the dissolution amount of zinc particles in the process of water bath for phase change, ensuring the zinc equivalent of the filter membrane products, and obtaining a concentration that inhibits microorganisms. For example, the filter membrane of the nano-zinc particles prepared by the present invention can reach the standard of more than 600 ppm per unit particle.

Referring to FIG. 9, which shows a first test report, the test date is Feb. 9, 2015, and it can be known from the test result that a plastic masterbatch made from the zinc containing plastic solvent of the present invention has zinc content per unit up to 12,700 ppm.

Referring to FIG. 10, which shows a second test report, the test date is Apr. 27, 2015, and it can be known from the test result that a hollow silk film made of the plastic masterbatch having nano-zinc particles of the present invention has the zinc content up to 851 ppm.

Referring to FIG. 11, which shows a third test report, the test date is Sep. 30, 2015, and it can be known from the test result that a PS hollow silk film made of the plastic masterbatch having nano-zinc particles of the present invention has zinc content up to 845 ppm.

Therefore, it can be known from the above three test reports that the method for making a filter membrane still can have similar or close results even under the same construction method, the same formula, different time and different equipment condition, which proves that the plastic masterbatch having nano-zinc particles of the present invention is repeatable; it is undoubted that the present invention has this advantage.

Referring to FIG. 12, which shows a fourth test report, the test date is Sep. 30, 2016; it can be known from the test result that the amount of zinc elements washed from the plastic masterbatch having nano-zinc particles is only 3 ppm in the process of casting solution phase transition water bath; the instrument can not detect if the washed zinc element is less than 2 ppm according to this test method. So, it can be concluded form the test data that zinc elements are not easy to be washed out from the plastic masterbatch having nano-zinc particles of the present invention, and most of them are remained in fiber film silk; the detected washed-out zinc amount 3 ppm can be proved to be quite low.

The filter membrane having nano-zinc particles so made can be used for the filtration of liquid or gas; zinc particle being antibacterial allows the filter membrane having nano-zinc particles to be capable of decomposition of bacteria and inhibition of bacterial growth. In addition, nano-zinc particles being stably linked with polymer material allows nano-zinc particles not to be easy to be lost gradually from the filter membrane having nano-zinc particles after water wash, capable of maintaining the antibacterial capacity of the filter membrane effectively.

It is worth noting that the filter membrane having nano-zinc particles of the present invention being capable of inhibiting bacterial growth is using a constant 3.3 eV power gap carried by nano-zinc oxide to force the extracellular molecules of microbial bacteria or ammonia molecules to break when the nano-zinc oxide is in contact with microbial bacteria or ammonia molecules to cause, for example, mechanisms such as the metabolism, nutrition in the outer membrane of bacteria to be lost, and thus to promote cell death, thereby achieving the decomposition of bacterial and inhibition of bacterial growth.

Furthermore, the power gap will cause water molecules $H_2O$ in the air to be free when the filter membrane having nano-zinc particles of the present invention is applied to the filtration of ammonia gas molecules; this kind of reaction needs $H_2O$ to participate to form (—OH) radicals, which will react with $NH_3$ to take H away from it to form $NH_2$— gradually, and finally, N is further in combination with other N to form a stable $N_2$ molecule, the decomposition formula of the entire $NH_3$ is shown as the following:

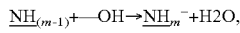
$NH_{(m-1)} + $—$OH \rightarrow NH_m^- + H2O$, and finally, the free nitrogen atom will be in combination with a nitrogen atom: $N+N \rightarrow N2$ to form nitrogen gas.

We claim:

1. A method for manufacturing a filter membrane for inhibiting microorganisms, comprising the following steps:
    (a) obtaining a nano-zinc precursor, and dissolving said nano-zinc precursor into water;
    (b) adding at least one reducing agent and at least one interfacial agent in said water dissolved with said nano-zinc precursor, thereby reducing zinc ions of said nano-zinc precursor to nano-zinc particles so as to form a liquid having nano-zinc particles;
    (c) respectively placing said liquid having nano-zinc particles and a polymer material into plastic masterbatch process equipment by means of melt grafting, respectively processing said liquid having nano-zinc particles and said polymer material to be in a volatile state with said plastic masterbatch process equipment, mixing and linking said volatilized liquid having nano-zinc particles with said volatilized polymer material in the process of air extraction, and adding at least one grafting agent to perform a mixed graft link so as to form a plastic masterbatch having nano-zinc particles; and
    (d) making said plastic masterbatch having nano-zinc particles into a filter membrane having nano-zinc particles through film making equipment.

2. The method according to claim 1, wherein said nano-zinc precursor is zinc chloride, zinc gluconate, zinc acetate, zinc sulfate or zinc carbonate.

3. The method according to claim 1, wherein said reducing agent is one or more than one selected from a group constituted by hydrazine compounds, dextrose, sodium ascorbate and ascorbic acid, sodium carboxymethyl cellulose (CMC), $SO_2$ and $NaBH_4$.

4. The method according to claim 1, wherein said interfacial agent is one or more than one selected from a group constituted by cetyl trimethylammonium bromide (CTAB), sodium dodecyl sulfate (SDS), polyvinylpyrrolidone (PVP), 3-(trimethoxysilyl)propyl methacrylate, MSMA, sodium hydrogen, methylsul foliate, dibenzoyl-L-tartaric acid (DBTA), 3-aminopropyltrimethoxy-silane (APTMS), and (3-mercaptopropyl)trimethoxysilane (MPTMS).

5. The method according to claim 1, wherein said polymer material is PET, PA6, PP, PE, ABS, PC, PVDF, PS, PES, PVC or PAN.

6. The method according to claim 1, wherein in said step (c) of respectively placing said liquid having nano-zinc particles, said melt grafting is to place said liquid having nano-zinc particles and a polymer material respectively in a plastic masterbatch process equipment having twin screw extrusion mechanism and at least six suction holes, said twin screw extrusion mechanism being in a vacuum state; said liquid having nano-zinc particles and polymer material are respectively placed in said plastic masterbatch process equipment, said liquid having nano-zinc particles and polymer material having a weight ratio ranged between 1:10 and 1:1; said liquid having nano-zinc particles and polymer material are respectively processed to be in a volatile state with said plastic masterbatch process equipment, allowing said volatilized liquid having nano-zinc particles and volatilized polymer material to be mixed and linked together through said twin screw extrusion and six suction holes in the process of air extraction; and at this point, at least one grafting agent is added therein to perform mixing, grafting and linking, thereby forming a plastic masterbatch having nano-zinc particles.

7. The method according to claim 1, wherein in said step (b) of adding at least one reducing agent, the manner of zinc ions of said nano-zinc precursor being reduced to said nano-zinc particles is to place zinc ions of $Zn^{+2}$ concentration ranged from $1 \times 10^{-5}$ mole to $1 \times 10^{-3}$ mole in a glass bottle, deionized water (DI) is added in said glass bottle, and the concentration of sodium dodecyl sulfate the (SDS) is set to be ranged from 1 mM to 10000 mM, the concentration of cetyltrimethylammonium bromide (CTAB) from 1 mM to 10000 mM, the concentration of sodium carboxymethylcellulose (CMC) from 1 to 20 wt %; a solution in which a reducing agent $Na_2S_2O_5$ is ranged from 1 to 5 gams and a strong reducing agent $NaBH_4$ from 0.01 to 10M is added after stirred uniformly with a heating stirrer; in the process of stirring, said reducing agents are respectively added in; if said reducing agent has a high pH value, 0.1 to 40 μl of concentrated hydrochloric acid is needed to drop in; at this point, the pH value of said solution is adjusted to about 1 to 5, and said solution is stirred continuously and placed into a hot water bath of temperature ranged from 50 to 90 degrees centigrade, and heated and stirred with a magnet electric heating stirrer, thereby reducing nano-zinc ions to nano-zinc particles.

8. The method according to claim 1, wherein in said step (b) of adding at least one reducing agent, the manner of zinc ions of said nano-zinc precursor being reduced to the nano-zinc particles uses a sonochemical method; said nano-zinc precursor is placed in a reaction bottle, and said reaction bottle is then placed in a ultrasonic oven, using ultrasonic oscillation to generate reduced free radicals to reduce metal ions so as to generate nano-zinc particles; metal salt aqueous solution is then placed in said reaction bottle, and said interfacial agent is added therein to stabilize said nano-zinc particles; said reaction bottle is placed in a ultrasonic oscillator and oscillated thereby, and a reaction is completed after 8 to 15 minutes is completed to reduce nano-zinc ions to nano-zinc particle.

9. The method according to claim 1, wherein in said step (b) of adding at least one reducing agent, said manner of zinc ions of said nano-zinc precursor being reduced to said nano-zinc particles uses an electrochemical method for generating metal nano-particles, the sizes of said nano-particles can be adjusted by controlling the current of electrolytic apparatus; thereby reducing said zinc ions of said nano-zinc precursor to said nano-zinc particles with said electrochemical method.

10. The method according to claim 1, wherein said grafting agent is maleic anhydride, acetic anhydride, glycidyl methacrylate, acrylamide or acrylic acid.

11. The method according to claim 1, therein said filter membrane having nano-zinc particles is a hollow fiber filter membrane, plate filer membrane.

* * * * *